United States Patent [19]

Biswas

[11] Patent Number: 5,386,836
[45] Date of Patent: Feb. 7, 1995

[54] URINARY INCONTINENCE DEVICE

[75] Inventor: Nicholas Biswas, New South Wales, Australia

[73] Assignee: Zedlani Pty Limited, Parramatta, Australia

[21] Appl. No.: 89,422

[22] Filed: Jul. 9, 1993

Related U.S. Application Data

[63] Continuation of Ser. No. 695,441, May 3, 1991, abandoned, which is a continuation-in-part of Ser. No. 448,166, Dec. 8, 1989, Pat. No. 5,036,867, which is a continuation-in-part of Ser. No. 108,276, Oct. 13, 1987, Pat. No. 4,920,986.

[30] Foreign Application Priority Data

| Oct. 14, 1986 | [AU] | Australia | PH8486 |
| May 3, 1990 | [AU] | Australia | PJ9967 |
| Oct. 25, 1990 | [AU] | Australia | PK3010 |

[51] Int. Cl.⁶ ............................. A61F 2/00
[52] U.S. Cl. ................. 128/885; 128/DIG. 25; 600/29; 600/30
[58] Field of Search ................. 600/28–30; 128/831, 833, 839, 885, DIG. 25

[56] References Cited

U.S. PATENT DOCUMENTS

| 1,790,801 | 2/1931 | Dickstein . | |
| 2,602,444 | 7/1952 | Stanford | 128/885 |
| 2,649,086 | 8/1953 | Sluijter | 128/1 |
| 3,554,184 | 1/1971 | Habib | 600/29 |
| 3,646,929 | 3/1972 | Bonnar | 600/29 |
| 3,705,575 | 12/1972 | Edwards | 600/29 |
| 3,768,102 | 10/1973 | Kwan-Gett et al. | 128/DIG. 25 |
| 3,841,304 | 10/1974 | Jones | 600/29 |
| 4,019,498 | 4/1977 | Hawtrey et al. | 600/29 |
| 4,139,006 | 2/1979 | Corey | 128/127 |
| 4,139,007 | 2/1979 | Diamond | 128/885 X |
| 4,200,090 | 4/1980 | Drobish | 128/837 X |
| 4,292,965 | 10/1981 | Nash et al. | 128/833 |
| 4,381,771 | 5/1983 | Gabbay | 128/837 X |
| 4,553,972 | 11/1985 | Vickery | 128/833 X |
| 4,749,186 | 6/1988 | Harding-Randle | 128/DIG. 25 |
| 4,821,741 | 4/1989 | Mohajer | 128/837 |
| 4,858,624 | 8/1989 | Shihata | 128/837 X |
| 4,920,986 | 5/1990 | Biswas | 128/885 |
| 4,969,902 | 11/1990 | Ravo | 600/30 X |
| 5,007,894 | 4/1991 | Enhorning | 600/29 |
| 5,036,867 | 8/1991 | Biswas | 600/30 X |

FOREIGN PATENT DOCUMENTS

| 0006609 | 1/1980 | European Pat. Off. | 128/837 |
| 3720858 | 6/1987 | Germany . | |

*Primary Examiner*—Randall L. Green
*Assistant Examiner*—Elizabeth M. Burke
*Attorney, Agent, or Firm*—Ladas & Parry

[57] ABSTRACT

An intra-vaginal urinary incontinence device basically comprises a resilient base portion (31), and a bladder support portion (40) extending away from the base portion (31) and having two opposed projections having a support section (30) therebetween forming a cradle (32) which receives and supports the neck of the bladder. The base portion is flexible to allow insertion into the vagina and the size and position of the cradle can be varied for different patients. The two projections may extend from the base portion directly or be formed on the end of a stalk and the support section is preferably arranged above the plane of the base portion.

18 Claims, 5 Drawing Sheets

URINARY INCONTINENCE DEVICE

This is a continuation of copending application Ser. No. 07/695,441 filed on May 3, 1991 now abandoned, which is a continuation-in-part of co-pending U.S. patent application Ser. No. 07/448,166 filed Dec. 8, 1989 and now U.S. Pat. No. 5,036,867 granted Aug. 6, 1991, which is a continuation-in-part of U.S. patent application Ser. No. 07/108,276 filed Oct. 13, 1989 and now U.S. Pat. No. 4,920,986 granted May 1, 1990.

BACKGROUND OF THE INVENTION

The present invention relates to devices for controlling urinary incontinence and vaginal and rectal prolapse in females. Particularly, the invention relates to a device which may be removably inserted into the vagina.

Female urinary incontinence is a common problem and is particularly prevalent where damage to the bladder or neck of the bladder has occurred during child birth. In elderly female patients, urinary incontinence is wide spread.

In normal continent patients, in the erect posture, there is no descent of the bladder neck below the pelvic floor muscle, thereby equal distribution of intra-abdominal pressure to the bladder and bladder neck and pelvic urethra occurs and continence is maintained. However, in stress incontinence this is lost due to descent of the bladder neck below the pelvic floor muscle. On coughing or sneezing or physical exercise, i.e. when strain is put upon the bladder, an involuntary spurt of urine is released from the bladder. This involuntary urine release is unpleasant and embarrassing. The released urine may irritate the groin region and result in an offensive odour.

Vaginal and rectal prolapse are quite common conditions in females, particularly those who have vaginally delivered one or more children. These conditions may be painful, and uncomfortable. Additionally, sexual intercourse may be impaired by occlusion of the vagina.

It is a generally accepted view that surgical treatment is most appropriate for cure of stress incontinence and vaginal and rectal prolapse. However, in elderly or infirm patients the risk of surgery is too great, so that often these conditions go untreated.

Previously proposed devices to treat incontinence and avoid recourse to surgery have generally been unsatisfactory. Particularly, they are cumbersome, difficult to use, need to be replaced frequently, are inadequate in cases of permanent incontinence and often fail to prevent involuntary urinary leakage.

A previously known intra-vaginal device for controlling urinary incontinence in females is disclosed in U.S. Pat. No. 4,139,006. This previously known device has as its object the deflection of the urethra. More particularly it has the object of displacing a surface of the superior wall of the vagina and intermediate sections of the urethra adjacent thereto, toward the pubic bone, to reduce the urethro-visicle angle to restore the patient's natural control over the flow of urine through the urethra from the bladder to the urethral opening. The device has a pair of forward projections which lie on either side of urethra intermediate portion and apply a force thereto to deflect the intermediate portion of the urethra towards the pubic bone.

Another known intra-vaginal device is disclosed in European Patent Specification No. 0 264 258 filed in the name of the present applicant. In this specification there is described a generally U-shaped device having a pair of resilient opposed limbs connected by a flexible base portion so that one of the limbs lies adjacent the posterior vaginal wall and the other limb, which is provided with a cradle-like structure for lifting the bladder base and neck, lies adjacent the anterior vaginal wall, the resiliency of the base portion being such as to bias the two limbs apart and into engagement with the walls of the vagina. Clearly, however, such devices which bias against the wall of the vagina can cause pain or irritation to the vaginal wall and, in order to mitigate this, must be very carefully matched in size to the vagina of the patient concerned. This is both costly and time consuming.

In a still further known intra-vaginal device for controlling urinary incontinence, as described in PCT Patent Specification No. WO 89/09582, also filed by the present applicant, there is proposed a substantially cup-shaped annulus of resilient material having a pair of rearwardly-extending, vaginal wall-engaging projections and a pair of forwardly and upwardly extending projections defining a cradle therebetween for receiving the bladder neck. Although the annulus can be made to be either planar or cup-shaped, the annulus must be sufficiently resilient to be deformed within the vagina into a cup-shape. Thus, once again, the vaginal walls must bias the device at a few discrete points of engagement, which can cause pain or irritation.

BRIEF SUMMARY OF THE INVENTION

It is therefore an object of the present invention to provide an intra-vaginal device to aid in controlling urinary incontinence which overcomes, or at least reduces the above disadvantages.

Accordingly, the invention provides, in one aspect, an entirely intra-vaginal urinary incontinence device comprising a resilient generally substantially planar circular base portion having integrally formed thereupon a bladder support portion extending away from the plane of the base portion, the bladder support portion being provided with a cradle for receiving and supporting, directly or indirectly, the neck of a bladder of a patient in a raised position, and wherein the base portion is sufficiently flexible to be inserted into the vagina of the patient, but sufficiently resilient that it returns to a substantially planar configuration when in position in the vagina.

In preferred embodiments, the base portion is annular or toroidal, thereby defining a central aperture which, in use, lies adjacent the patient's cervix. The bladder support portion preferably extends radially outwardly from the base portion. The cradle is preferably formed by two projections having a bridge section therebetween. It will be appreciated that the projections could extend directly from the base portion with the bridge section being formed either by the base portion or, depending on the length of the projections, at a distance from the base portion, or the two projections could be formed on an end of the bladder support portion away from the base portion.

According to a second aspect of the present invention, there is provided an entirely intra-vaginal urinary incontinence device comprising a resilient generally substantially planar base portion having integrally formed thereupon a bladder support portion extending away from the base portion, the bladder support portion being provided with a support element arranged away from the plane of the base portion for supporting, directly or indirectly, the neck of a bladder of a patient.

In a preferred embodiment, the support element comprises a cradle comprising two opposed projections having a bridge section therebetween, the bridge section being away from the plane of the base portion. It will be apparent that, depending on the height of the projections, the bridge section can be integral with the base portion or can be separate therefrom, extending between the two projections at a distance from the plane of the base portion.

In a preferred embodiment, the support element extends away from the base portion in directions within and out of the plane of the base portion. Preferably, the support element comprises a longitudinal stalk having a cradle at an end thereof away from the plane of the base portion. The cradle preferably comprises two opposed projections extending away from the base portion in directions within and out of the plane of the base portion and a bridge section therebetween arranged away from the plane of the base portion.

BRIEF DESCRIPTION OF THE DRAWINGS

Various embodiments of urinary incontinence devices according to the invention will now be more fully described, by way of example, with reference to the drawings, of which.

DETAILED DESCRIPTION OF VARIOUS EMBODIMENTS OF THE INVENTION

Figure 1:
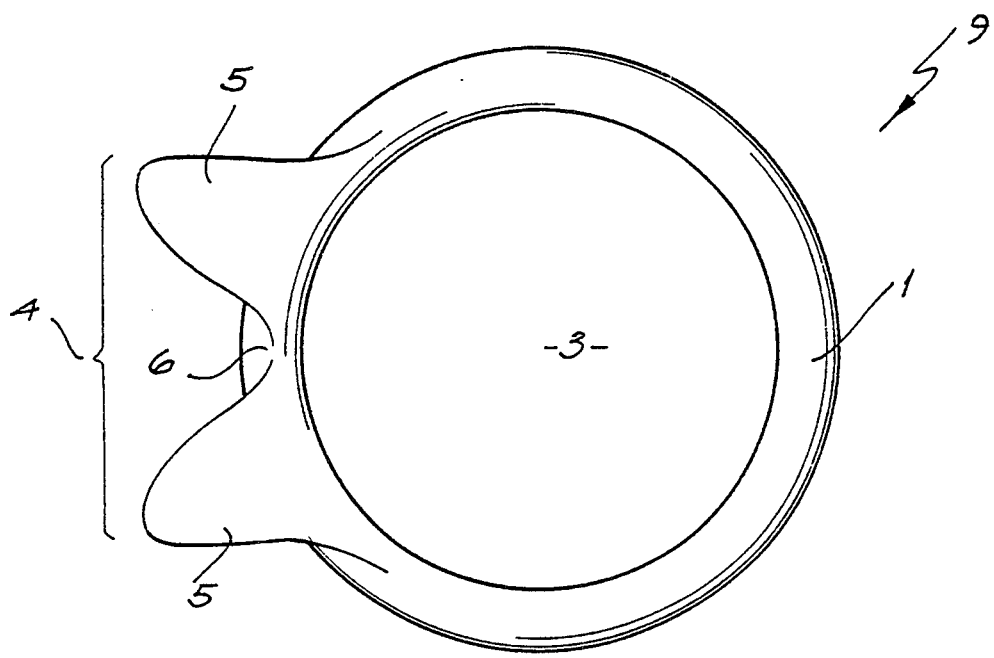
FIG. 1 is a top plan view of one embodiment of an intra-vaginal device according to one aspect of the invention.
Figure 2:
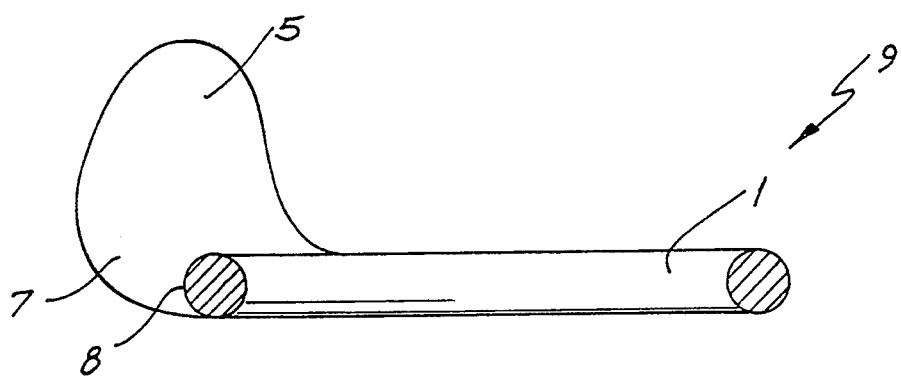
FIG. 2 is a cross-sectional view of the intra-vaginal device of FIG. 1.
Figure 3:
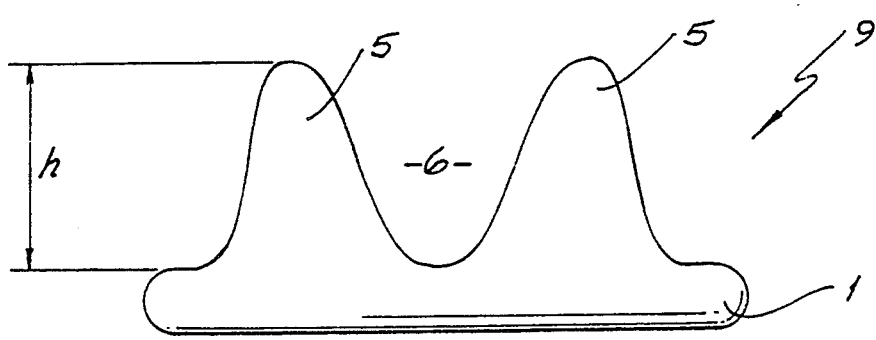
FIG. 3 is a front elevation of the intra-vaginal device of FIG. 1.

Thus, according to one aspect of the present invention there is shown in FIGS. 1 to 3 an intra-vaginal device 9 constructed of a flexible material, for example a plastic/silicone compound. As shown in FIG. 1, the device 9 comprises a base portion 1 which is of an annular form.

Although the base portion 1 forms an annulus or ring, the ring need not be exactly circular. The base 1 defines an aperture 3 which in use is adjacent the cervix of the uterus of the patient.

Also extending from and integrally formed in the base portion 1 is a forward portion 4 which includes a pair of upwardly extending projections 5 which are intended to engage the anterior vaginal wall to lift the bladder adjacent the bladder neck. The projections 5 are about 2 cm high. Other heights may be required, depending on size and shape of the vagina of the particular patient. Depending upon the needs of the individual patient, a height h, as shown in FIG. 3, of the projections should be about 3–5 cm above the height of the top surface 16 of the annulus 11. A height h of about 36 mm has been shown to be useful in a number of patients.

Defined between the projections 5 is a cradle 6 within which the bladder neck lies to be cradled thereby. The cradle 6 is shown more clearly in FIG. 3. It should be appreciated that the pressures applied to the bladder neck are minimized by the cradle neck 6. Note with reference to FIG. 2 that a portion 7 of the projections 5 preferably extends forward of the outer periphery 8 of the base 1.

The base portion 1 may be inherently resilient or may contain a resilient insert. The resiliency of the material forming the base portion is chosen such that the device is flexible enough that it can be easily inserted into the vagina, but sufficiently rigid that, once in position within the vagina, the base portion reverts to its substantially circular shape. The circular shape means that any stress between the base portion and the vaginal walls is substantially equalised over the whole of the annular portion so that no one area of the vaginal wall is much more stressed than other areas. Of course, some variations will occur, but the circular shape reduces the variations, thereby reducing the amount of pain or irritation felt in any one area of the vaginal wall. This is particularly so when the base portion is of toroidal shape, as shown in FIGS. 1 and 2 of the drawings.

The device may be of different sizes to accommodate different vaginal size. For example, the diameter of the base portion can increase in increments of 5 mm from about 55 mm to 105 mm, preferably, from 55 mm to 85 mm. The base portion itself can be of any suitable height, but a height of about 6 mm has been found to be satisfactory. If the base portion is a torus, this would be the diameter of the structure forming the torus. Preferably, those portions of the device contacting the vaginal wall are smeared with Disaestrol and Sultril cream in order to minimize vaginal irritation.

In a preferred embodiment, the annular base portion 1 is substantially planar, but may in some instances be slightly curved in one or two planes for better fit and resiliency.

Figure 4:
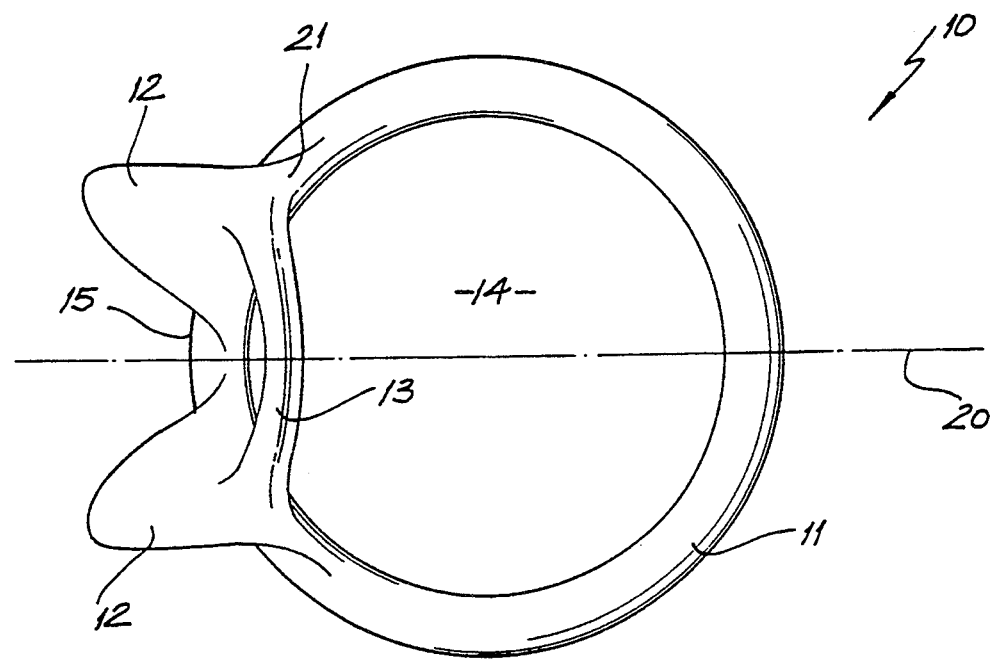
FIG. 4 is a top plan view of one embodiment of an intra-vaginal device according to another aspect of the present invention.

In a further aspect of the present invention, as shown in FIG. 4, an entirely intra-vaginal device to aid in controlling urinary incontinence 10 comprises a resilient annulus 11 having integrally formed thereupon a pair of upwardly extending projections 12. An integral bridging element 13 extends between the projections 12. The device 10 is formed of resilient material so that it may be resiliently deformed within the vagina so as to be biased outward and into contact with the posterior and anterior vaginal walls. In the alternative, the device, in use, may rest on the pelvic floor muscle. The device is about 8 cm in diameter. The device preferably includes a central aperture 14 to allow for the discharge of menstrual blood and vaginal secretions.

Figure 5:
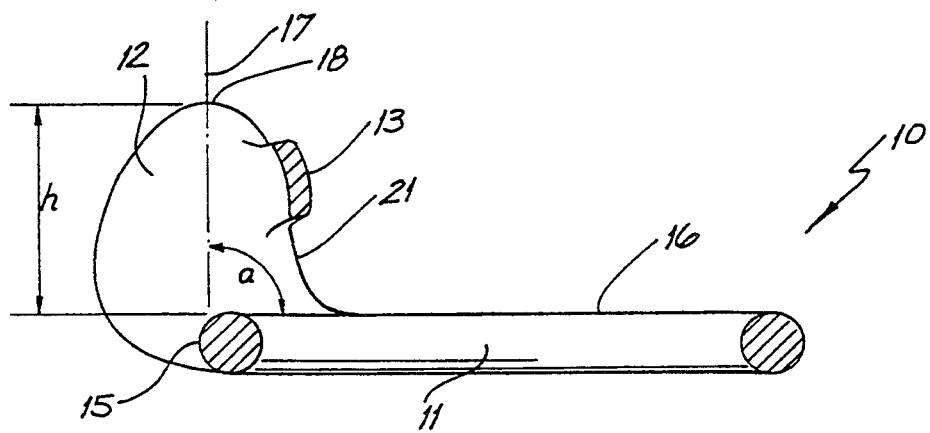
FIG. 5 is a cross sectional view of the device depicted in FIG. 4.

As shown in FIG. 5, the projections 12 preferably extend both upwardly from the annulus 11 and forwardly of the front of the annulus 15. Depending upon the needs of the individual patient, the height h of the projections should be about 1.5–5 cm above the height of the top surface 16 of the annulus 11. A height h of about 36 mm has been shown to be useful in a number of patients. Further, the projections 12 may be inclined relative to the annulus 11. The projections may be inclined between about 90° and 135° with respect to the annulus 11 as described by the angle a between the plane of the annulus (or its tangent if curved) and an imaginary axis 17 of the projections 12 which axis 17 passes through the uppermost tip 18 of the projections 12.

Figure 6:
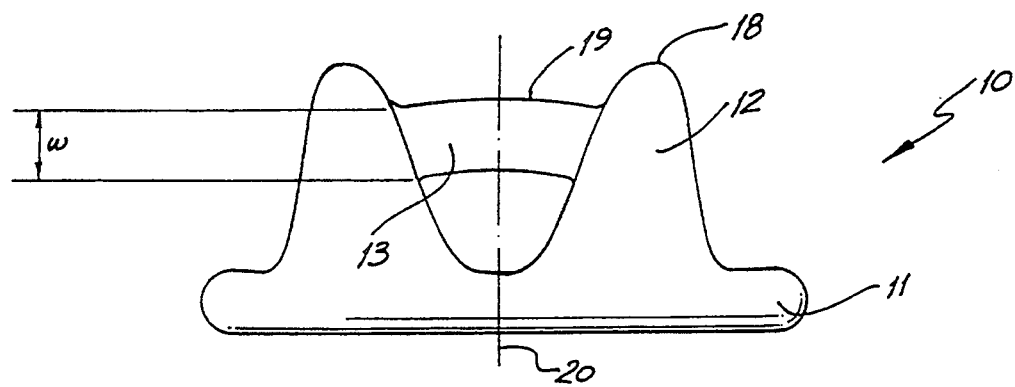
FIG. 6 is a front elevation of the device depicted in FIG. 4.

As shown in FIG. 6, the upper surface 19 of the bridge element 13 should be displaced about 1–1.5 cm from the tip 18 of the extensions 12. This displacement forms a recess between the tips of the extensions, which recess accommodates the urethra.

Unlike other known devices, this embodiment of the present invention is characterized by the bridging element 13. A bridging element is defined as a projection or body which lies in a medial plane 20, which body is elevated above a supporting platform such as an annulus. The purpose of the bridging element is to enhance the support offered to the bladder neck, allowing the bladder neck to be elevated higher than in other known devices. From this definition it should be appreciated that a bridging element may be used in conjunction with a wide variety of supporting structures such as the resilient annulus 11, and may extend between a wide variety of upwardly extending projections, such as the upwardly and forwardly projections 12 of the present invention. In particular, a bridging element may be integrally formed with upwardly extending projections of various heights, configurations, and angles of inclination. Further, the bridging element 13 as depicted in FIGS. 4–6 is shown as extending only between a portion of the posterior surfaces 21 of the projections or extensions 12. In actuality, the width w of the bridging element 13 may be increased so that it extends across substantially the entirety of the posterior surfaces 21 of the projections 12. In most instances, it will still be desirable to recess the top surface 19 of the bridging element 13 with respect to the tips 18 of the projections 12 as the recessed formed thereby would be considered useful, in most instances, for supporting and locating the urethra.

Figure 7:
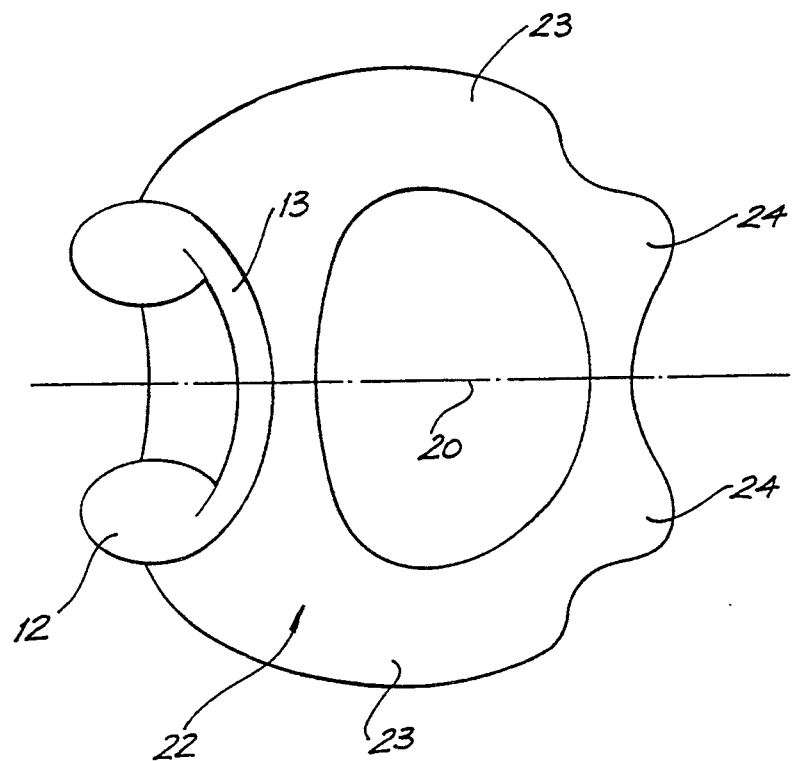
FIG. 7 is a top plan view of another embodiment of a device according to the present invention.

As previously explained, it is the bridging element which supports the bladder neck. As such, a wide variety of support structures or ring configurations may be utilisable in conjunction with the bridging element of the present invention. As shown in FIG. 7, a supporting annulus 22 may have additional structures such as side flanges 23 for engaging the sides of the vaginal wall to aid in retaining the device in position. The support structure may have any cross sectional shape or combine cross sections. Rearwardly extending portions 24 may also be optionally incorporated for engaging the posterior vaginal wall.

A further advantage of the bridging element is that it provides increased strength to the structure so that, when the device is distorted in order to be fitted into the vagina, the angle to which the two projections are spread, is limited.

Figure 8:
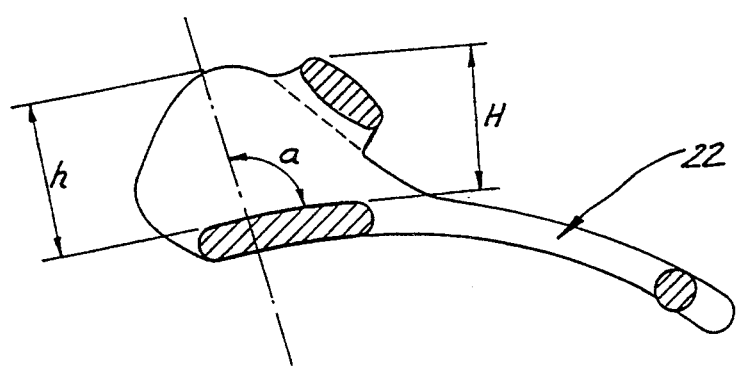
FIG. 8 is a cross sectional view of the device depicted in FIG. 7.

As previously explained in relation to FIGS. 1 to 3, although the base portion of the device is generally planar, this is intended to include embodiments such as that shown in FIG. 8, where the base portion is slightly cup-shaped or arcuate.

As shown in FIG. 8, the supporting annulus 22 may be arched, or if required, cup shaped. Arched or cupped configurations provide additional resilient biasing against the vaginal walls, when the device is in use. It should be appreciated when considering FIGS. 7 and 8 together, that by varying the angle of inclination a of the projections 12, the height of the projections h and the height H of the bridging element 13, the practitioner can provide a wide variety of bladder neck support configurations to suit a wide variety of patient needs.

Figure 9:
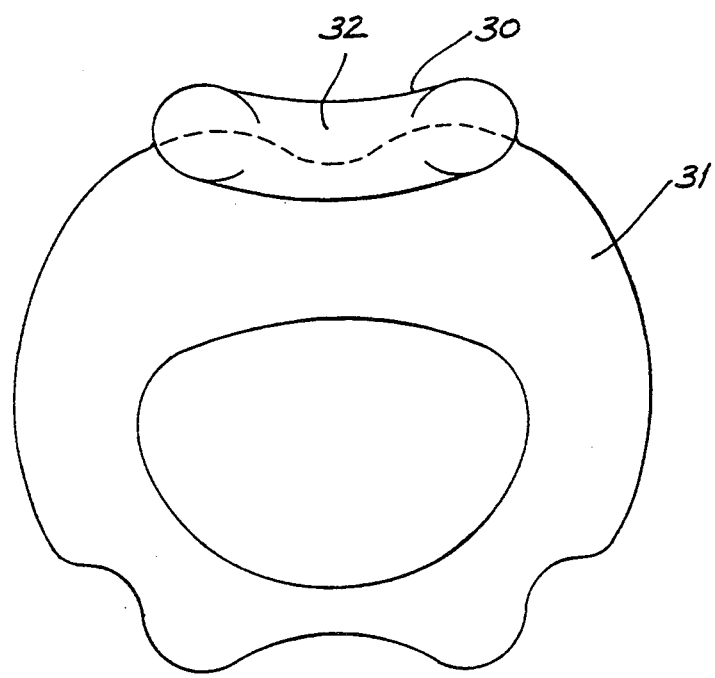
FIGS. 9, 10, and 11 are top plan views of alternate embodiments of the present invention.
Figure 10:
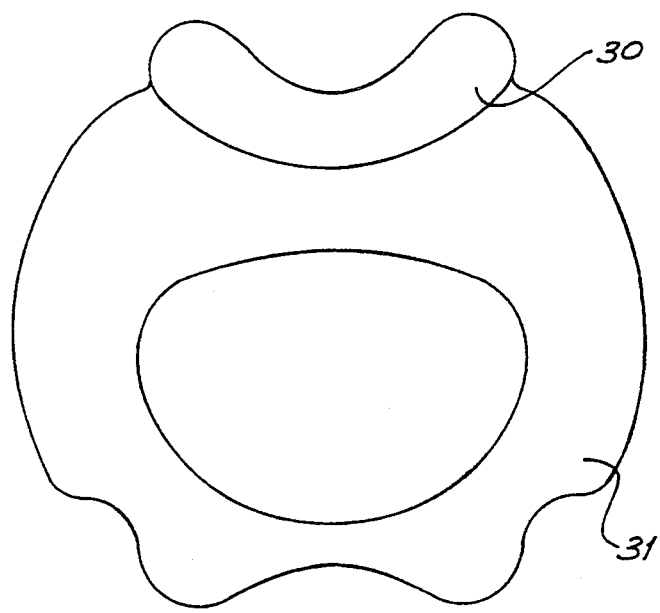
Figure 11:
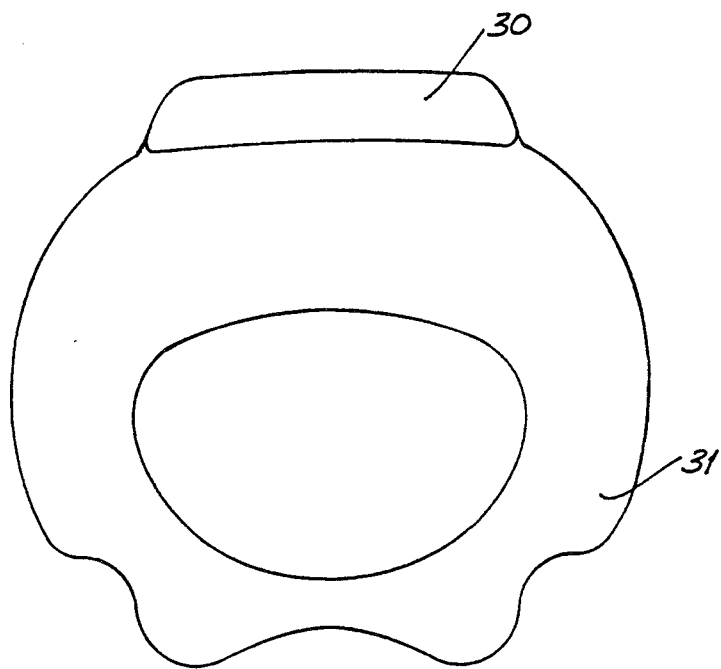
Figure 12:
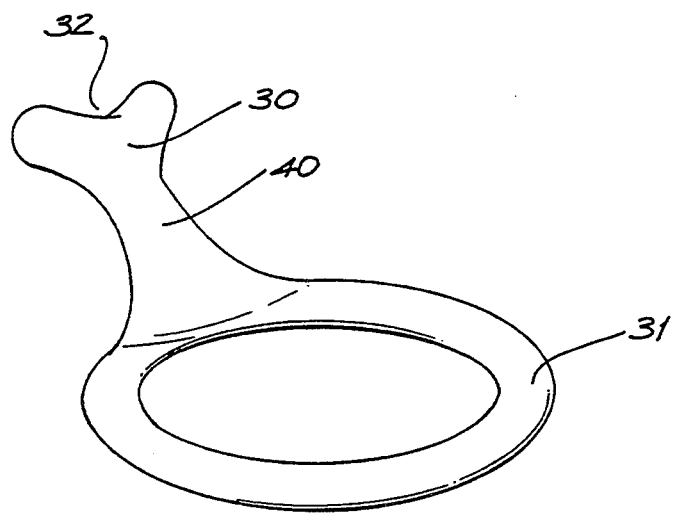
FIG. 12 is a perspective view of another device according to the present invention.

Consistent with the previous description of the medial bridging element, it will be understood, with reference to FIG. 9, 10, 11 and 12 that the pair of upwardly extending projections are not essential for supporting such a bridge element. As shown in FIGS. 9 to 12, the bridge element 30 may consist of a single unitary structure which projects above the plane or curvature of the supporting annulus 31. The bridge element 30 may be curved slightly as shown in FIG. 9, curved substantially as shown in FIG. 10, or relatively flat as shown in FIG. 11. In most instances, it will be preferred to provide a recess 32 on the upper surface of the bridge element 30 in which the urethra may seat. As shown in FIG. 12, the bridge element 30 is supported above the annulus 31 by a single stalk 40 which extends above the level of the annulus 31. The stalk may extend forwardly, as required.

While the structure of the bridge element of the present invention has been disclosed with reference to an integral fabrication, it will be understood that both the bridge element and extending projections (where utilized) may be provided as continuously or incrementally adjustable. As such, both the height h of the projections and the height H of the bridge element may be adjusted to suit the needs of different patients. This would serve as an alternative to providing a variety of integrally formed devices, one of which would be selected for a particular patient. The various examples of sizes and shapes of the base portion described above with reference to FIGS. 1 to 3 are equally applicable to some embodiments of this aspect of the invention.

While the present invention has been described with reference to particular configurations and details of construction, these should be understood as having been provided by way of example and not as limitations to the scope or spirit of the invention.

What I claim is:

1. In an entirely intra-vaginal urinary incontinence device comprising a resilient circular base portion of a planar configuration defining a plane, an improvement wherein:

said circular base portion has integrally formed thereupon a bladder support portion extending away from the plane of the base portion, the bladder support portion forming a cradle for receiving and supporting, at least indirectly, a neck of a bladder of a patient in raised position, and the base portion being flexible so as to be insertable into a vagina of the patient, but resilient so that it returns to the planar configuration when in position in the vagina, wherein the cradle is formed by two projections having a bridge section therebetween.

2. An entirely intra-vaginal urinary incontinence device according to claim 1, wherein the projections extend directly from the base portion with the bridge section being integrally coupled to the base portion.

3. An entirely intra-vaginal urinary incontinence device according to claim 1, wherein the projections extend directly from the base portion with the bridge section being provided at a distance from the base portion.

4. An entirely intra-vaginal urinary incontinence device according to claim 1, wherein the two projections are formed on an end of the bladder support portion away from the base portion.

5. In an entirely intra-vaginal urinary incontinence device comprising a resilient substantially planar base portion defining a plane, an improvement wherein:
the base portion has integrally formed thereupon a bladder support portion extending away from the plane of the base portion, the bladder support being provided with a support element located on one side of the plane of the base portion for supporting, at least indirectly, a neck of a bladder of a patient,
wherein the support element comprises a cradle comprising two opposed projections having a bridge section therebetween, the bridge section being away from the plane of the base portion.

6. An entirely intra-vaginal urinary incontinence device according to claim 5, wherein the bridge section is integrally coupled to the base portion.

7. An entirely intra-vaginal urinary incontinence device according to claim 5, wherein the bridge section is separate from the base portion, extending between the two projections at a distance from the plane of the base portion.

8. In an entirely intra-vaginal urinary incontinence device comprising a resilient substantially planar base portion defining a plane, an improvement wherein:
the base portion has integrally formed thereupon a bladder support portion extending away from the plane of the base portion, the bladder support being provided with a support element located on one side of the plane of the base portion for supporting, at least indirectly, a neck of a bladder of a patient,
wherein the support element extends away from the base portion in directions within and out of the plane of the base portion.

9. In an entirely intra-vaginal urinary incontinence device comprising a resilient substantially planar base portion defining a plane, an improvement wherein:
the base portion has integrally formed thereupon a bladder support portion extending away from the plane of the base portion, the bladder support being provided with a support element located on one side of the plane of the base portion for supporting, at least indirectly, a neck of a bladder of a patient,
wherein the support element comprises a longitudinal stalk having a cradle at an end thereof away from the plane of the base portion.

10. An entirely intra-vaginal urinary incontinence device according to claim 9, wherein the cradle comprises two opposed projections extending away from the base portion in directions within and out of the plane of the base portion and a bridge section therebetween arranged away from the plane of the base portion.

11. In an entirely intra-vaginal urinary incontinence device comprising a resilient substantially planar circular base portion defining a plane, an improvement wherein:
the base portion has integrally formed thereupon a bladder support portion extending away from the plane of the base portion, the bladder support portion forming a cradle for receiving and supporting, at least indirectly, a neck of a bladder of a patient in a raised portion; and the base portion being flexible so as to be insertable into a vagina of the patient, but resilient so that it returns to a substantially planar configuration when in position in the vagina, wherein the base portion is toroidal, thereby defining a central aperture which, in use, lies adjacent to a cervix of the patient;
wherein the cradle is formed by two projections having a bridge section therebetween.

12. An entirely intra-vaginal urinary incontinence device according to claim 11, wherein the projections extend directly from the base portion with the bridge section being formed by the base portion.

13. An entirely intra-vaginal urinary incontinence device according to claim 11, wherein the projections extend directly from the base portion with the bridge section being provided at a distance from the base portion.

14. An entirely intra-vaginal urinary incontinence device according to claim 11, wherein the two projections are formed on an end of the bladder support portion away from the base portion.

15. In an entirely intra-vaginal urinary incontinence device comprising a resilient substantially planar circular base portion defining a plane, an improvement wherein:
the base portion has integrally formed thereupon a bladder support portion extending substantially perpendicularly away from the plane of the base portion, the bladder portion forming a cradle for receiving and supporting, at least indirectly, a neck of a bladder of a patient in a raised position, and the base portion being flexible so as to be insertable into a vagina of the patient, but resilient so that it returns to a substantially planar configuration when in position in the vagina,
wherein the cradle is formed by two projections having a bridge section therebetween.

16. An entirely intra-vaginal urinary incontinence device according to claim 15, wherein the projections extend directly from the base portion with the bridge section being formed by the base portion.

17. An entirely intra-vaginal urinary incontinence device according to claim 15, wherein the projections extend directly from the base portion with the bridge section being provided at a distance from the base portion.

18. An entirely intra-vaginal urinary incontinence device according to claim 15, wherein the two projections are formed on an end of the bladder support portion away from the base portion.

* * * * *